United States Patent [19]

McLaughlin et al.

[11] Patent Number: 5,789,542
[45] Date of Patent: Aug. 4, 1998

[54] AMPHIPATHIC PEPTIDES

[75] Inventors: Mark L. McLaughlin, Baton Rouge, La.; Calvin L. Becker, Gurnee, Ill.

[73] Assignee: Board of Supervisors of Louisiana State University and Agricultural and Mechanical College, Baton Rouge, La.

[21] Appl. No.: 944,133

[22] Filed: Oct. 6, 1997

Related U.S. Application Data

[63] Continuation of Ser. No. 789,077, Feb. 3, 1997, abandoned, which is a continuation of Ser. No. 681,075, Jul. 22, 1996, abandoned, which is a continuation of Ser. No. 232,525, Apr. 22, 1994, abandoned.

[51] Int. Cl.$^6$ .................. C07K 7/08; C12N 1/06
[52] U.S. Cl. .................. 530/326; 514/14; 435/259
[58] Field of Search .................. 530/326; 514/14; 435/259

[56] References Cited

FOREIGN PATENT DOCUMENTS

| | | | |
|---|---|---|---|
| 9012866 | 11/1990 | WIPO | C12N 1/06 |
| 9301723 | 2/1993 | WIPO | A61K 37/02 |

OTHER PUBLICATIONS

L.A. Chung et al., "Fluorescence Studies of the Secondary Structure and Orientation of a Model Ion Channel Peptide in Phospholipid Vesicles," Biochemistry, vol. 31, pp. 6608–6616 (1992).
E. K. O'Shea et al., "X–ray Structure of the GCN4 Leucine Zipper, a Two–Stranded, Parallel Coiled Coil," Science, vol. 254, pp. 539–544 (1991).
N. E. Zhou et al., "Synthetic Model Proteins: The Relative Contribution of Leucine Residues at the Nonequivalent Positions of the 3–4 Hydrophobic Repeat to the Stability of the Two–Stranded α–Helical Coiled–Coil," Biochemistry, vol. 31, pp. 5739–5746 (1992).
C. L. Becker, "The Design, Synthesis and Structure–Function Studies of Highly Repetitive Amphiphilic Antibacterial Peptides and the Synthesis of Benz[f]indene for the Preparation of Novel Metallocenes," Louisiana State University (Baton Rouge) PdH Dissertation (May 1994) (unpublished).
A. Zier et al., "Polyethylene Glycol Board Benzyl–and Fluorenyl Derivatives as Solubilizing Side–Chain Protecting Groups in Peptide Synthesis," Tetrahedron Letters, vol. 35, pp. 1039–1042 (1994).
S. E. Blondelle et al., "Design of Model Amphiphatic Peptides Having Potent Antimicrobial Activities," Biochemistry, vol. 31, pp. 12688–12694 (1992).
W. F. DeGrado et al., "Conformationally Constrained α–Helical Peptide Models for Protein Ion Channels," Biopolymers, vol. 29, pp. 205–213 (1990).
Patel, Biochem. Soc. Trans. (1989) 17 (5) 931.
Bundgaard, Biochem. Soc. Trans (1989) 17(15) 947–949.
Jaradpour et al., Biophysical Journal 66 (2 part 2) p. A394 (1994 –Mar. 6–10).
Becker et al., Abstr. Pap. Am. Chem. Soc. vol. 206 (1–2) (1993). Orgn 447.

Primary Examiner—Cecilia J. Tsang
Assistant Examiner—Anish Gupta
Attorney, Agent, or Firm—John H. Runnels

[57] ABSTRACT

Minimalist lytic peptides are disclosed that may be readily synthesized on a large scale via a highly-convergent, solution-phase synthesis. The peptides are amphipathic, and are easy and inexpensive to synthesize via solution phase techniques. The peptides exhibit anti-bacterial properties at concentrations that are not lethal to normal mammalian cells. The peptides comprise multimers, i.e. two or more repeats, of certain heptads of amino acid residues. The heptads were designed to generate amphipathic peptides when the heptads are combined into multimers, and were further designed to be readily suited for convergent, solution-phase synthesis. The preferred heptads are described generically by one of the following four formulas, in which "Xps" denotes a positively charged amino acid at physiological pH, and in which "Xnp" denotes a nonpolar amino acid at physiological pH: (1) $Xps_1Xnp_1Xnp_2Xps_1Xnp_1Xnp_2Xps$, or (2) $XpsXnp_1Xnp_2Xps_1Xnp_1Xnp_2Xps_1$, or (3) $Xps_1Xnp_1Xnp_2XpsXps_1Xnp_1Xnp_2$, or (4) $XpsXps_1Xnp_1Xnp_2Xps_1Xnp_1Xnp_2$. Other heptads are also disclosed.

32 Claims, 5 Drawing Sheets

SEQUENCE LISTING ( 1 ) GENERAL INFORMATION:

( i i i ) NUMBER OF SEQUENCES: 54

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Lys Leu Ala Lys Lys Leu Ala
1               5

( 2 ) INFORMATION FOR SEQ ID NO:2:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Lys Leu Ala Lys Lys Leu Ala Lys Leu Ala Lys Lys Leu Ala
1               5                       10

( 2 ) INFORMATION FOR SEQ ID NO:3:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

Lys Leu Ala Lys Lys Leu Ala Lys Leu Ala Lys Lys Leu Ala Lys Leu
1               5                       10                      15

Ala Lys Lys Leu Ala
                20

( 2 ) INFORMATION FOR SEQ ID NO:4:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Lys  Leu  Ala  Lys  Leu  Ala  Lys  Leu  Ala  Lys  Lys  Leu  Ala  Lys  Leu
1              5                   10                       15

Ala  Lys  Lys  Leu  Ala  Lys  Leu  Ala  Lys  Lys  Leu  Ala
              20                        25
```

( 2 ) INFORMATION FOR SEQ ID NO:5:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Lys  Leu  Ala  Lys  Leu  Ala  Lys
1              5
```

( 2 ) INFORMATION FOR SEQ ID NO:6:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Lys  Leu  Ala  Lys  Leu  Ala  Lys  Lys  Leu  Ala  Lys  Leu  Ala  Lys
1              5                   10
```

( 2 ) INFORMATION FOR SEQ ID NO:7:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Lys  Leu  Ala  Lys  Leu  Ala  Lys  Lys  Leu  Ala  Lys  Leu  Ala  Lys  Leu
1              5                   10                       15

Ala  Lys  Leu  Ala  Lys
              20
```

( 2 ) INFORMATION FOR SEQ ID NO:8:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
Lys  Leu  Ala  Lys  Leu  Ala  Lys  Lys  Leu  Ala  Lys  Leu  Ala  Lys  Lys  Leu
1              5                   10                       15

Ala  Lys  Leu  Ala  Lys  Lys  Leu  Ala  Lys  Leu  Ala  Lys
              20                        25
```

( 2 ) INFORMATION FOR SEQ ID NO:9:

( i ) SEQUENCE CHARACTERISTICS:
 ( A ) LENGTH: 7 amino acids
 ( B ) TYPE: amino acid
 ( C ) STRANDEDNESS: single
 ( D ) TOPOLOGY: linear ( i i ) MOLECULE TYPE: peptide ( x i ) SEQUENCE DESCRIPTION: SEQ ID NO:9:

Lys Phe Ala Lys Phe Ala Lys
1               5

( 2 ) INFORMATION FOR SEQ ID NO:10:

( i ) SEQUENCE CHARACTERISTICS:
  ( A ) LENGTH: 14 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:10:

Lys Phe Ala Lys Phe Ala Lys Lys Phe Ala Lys Phe Ala Lys
1               5                           10

( 2 ) INFORMATION FOR SEQ ID NO:11:

( i ) SEQUENCE CHARACTERISTICS:
  ( A ) LENGTH: 21 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:11:

Lys Phe Ala Lys Phe Ala Lys Lys Phe Ala Lys Phe Ala Lys Lys Phe
1               5                           10                          15

Ala Lys Phe Ala Lys
               20

( 2 ) INFORMATION FOR SEQ ID NO:12:

( i ) SEQUENCE CHARACTERISTICS:
  ( A ) LENGTH: 28 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:12:

Lys Phe Ala Lys Phe Ala Lys Lys Phe Ala Lys Phe Ala Lys Lys Phe
1               5                           10                          15

Ala Lys Phe Ala Lys Lys Phe Ala Lys Phe Ala Lys
               20                      25

( 2 ) INFORMATION FOR SEQ ID NO:13:

( i ) SEQUENCE CHARACTERISTICS:
  ( A ) LENGTH: 21 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:13:

```
Leu Lys Leu Ala Leu Lys Leu Leu Lys Leu Ala Leu Lys Leu Leu Lys
1               5                   10                  15

Leu Ala Leu Lys Leu
                20
```

(2) INFORMATION FOR SEQ ID NO:14:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

```
Leu Lys Leu Gly Leu Lys Leu Leu Lys Leu Gly Leu Lys Leu Leu Lys
1               5                   10                  15

Leu Gly Leu Lys Leu Leu Phe Leu
                20
```

(2) INFORMATION FOR SEQ ID NO:15:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

```
Lys Ala Leu Lys Ala Leu Lys
1               5
```

(2) INFORMATION FOR SEQ ID NO:16:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

```
Lys Ala Leu Lys Ala Leu Lys Lys Ala Leu Lys Ala Leu Lys
1               5                   10
```

(2) INFORMATION FOR SEQ ID NO:17:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

```
Lys Ala Leu Lys Ala Leu Lys Lys Ala Leu Lys Ala Leu Lys Lys Ala
1               5                   10                  15

Leu Lys Ala Leu Lys
                20
```

(2) INFORMATION FOR SEQ ID NO:18:

(i) SEQUENCE CHARACTERISTICS:

(A) LENGTH: 28 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:18:

Lys Ala Leu Lys Ala Leu Lys Lys Ala Leu Lys Ala Leu Lys Lys Ala
1               5                   10                  15

Leu Lys Ala Leu Lys Lys Ala Leu Lys Ala Leu Lys
            20                  25

(2) INFORMATION FOR SEQ ID NO:19:

(i) SEQUENCE CHARACTERISTICS:
          (A) LENGTH: 7 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:19:

Lys Leu Gly Lys Lys Leu Gly
1               5

(2) INFORMATION FOR SEQ ID NO:20:

(i) SEQUENCE CHARACTERISTICS:
          (A) LENGTH: 14 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:20:

Lys Leu Gly Lys Lys Leu Gly Lys Leu Gly Lys Lys Leu Gly
1               5                   10

(2) INFORMATION FOR SEQ ID NO:21:

(i) SEQUENCE CHARACTERISTICS:
          (A) LENGTH: 21 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:21:

Lys Leu Gly Lys Lys Leu Gly Lys Leu Gly Lys Lys Leu Gly Lys Leu
1               5                   10                  15

Gly Lys Lys Leu Gly
            20

(2) INFORMATION FOR SEQ ID NO:22:

(i) SEQUENCE CHARACTERISTICS:
          (A) LENGTH: 28 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:22:

Lys Leu Gly Lys Lys Leu Gly Lys Leu Gly Lys Lys Leu Gly Lys Leu

```
          1               5                    10                  15
       Gly  Lys  Lys  Leu  Gly  Lys  Leu  Gly  Lys  Lys  Leu  Gly
                      20                  25
```

(2) INFORMATION FOR SEQ ID NO:23:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

```
       Lys  Lys  Leu  Ala
       1
```

(2) INFORMATION FOR SEQ ID NO:24:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

```
       Lys  Lys  Leu  Ala  Lys  Leu  Ala
       1                   5
```

(2) INFORMATION FOR SEQ ID NO:25:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

```
       Lys  Lys  Leu  Ala  Lys  Leu  Ala  Lys  Lys  Leu  Ala  Lys  Leu  Ala
       1                   5                              10
```

(2) INFORMATION FOR SEQ ID NO:26:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

```
       Lys  Lys  Leu  Ala  Lys  Leu  Ala  Lys  Lys  Leu  Ala  Lys  Leu  Ala  Lys  Lys
       1                   5                              10                       15
       Leu  Ala  Lys  Leu  Ala
                      20
```

(2) INFORMATION FOR SEQ ID NO:27:

(i) SEQUENCE CHARACTERISTICS:
        (A) LENGTH: 28 amino acids
        (B) TYPE: amino acid
        (C) STRANDEDNESS: single
        (D) TOPOLOGY: linear ( i i ) MOLECULE TYPE: peptide ( x i ) SEQUENCE DESCRIPTION: SEQ ID NO:27:

```
Lys Lys Leu Ala Lys Leu Ala Lys Lys Leu Ala Lys Leu Ala Lys Lys
1               5                   10                  15
Leu Ala Lys Leu Ala Lys Lys Leu Ala Lys Leu Ala
            20                  25
```

( 2 ) INFORMATION FOR SEQ ID NO:28:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:28:

```
Lys Ala Leu Lys Lys Ala Leu
1               5
```

( 2 ) INFORMATION FOR SEQ ID NO:29:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:29:

```
Lys Ala Leu Lys Lys Ala Leu Lys Ala Leu Lys Lys Ala Leu
1               5                   10
```

( 2 ) INFORMATION FOR SEQ ID NO:30:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:30:

```
Lys Ala Leu Lys Lys Ala Leu Lys Ala Leu Lys Lys Ala Leu Lys Ala
1               5                   10                  15
Leu Lys Lys Ala Leu
            20
```

( 2 ) INFORMATION FOR SEQ ID NO:31:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:31:

```
Lys Ala Leu Lys Lys Ala Leu Lys Ala Leu Lys Lys Ala Leu Lys Ala
1               5                   10                  15
Leu Lys Lys Ala Leu Lys Ala Leu Lys Lys Ala Leu
            20                  25
```

( 2 ) INFORMATION FOR SEQ ID NO:32:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:32:

```
Lys  Lys  Ala  Leu  Lys  Ala  Leu
1                   5
```

( 2 ) INFORMATION FOR SEQ ID NO:33:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:33:

```
Lys  Lys  Ala  Leu  Lys  Ala  Leu  Lys  Lys  Ala  Leu  Lys  Ala  Leu
1                   5                           10
```

( 2 ) INFORMATION FOR SEQ ID NO:34:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:34:

```
Lys  Lys  Ala  Leu  Lys  Ala  Leu  Lys  Lys  Ala  Leu  Lys  Ala  Leu  Lys  Lys
1                   5                           10                          15

Ala  Leu  Lys  Ala  Leu
                    20
```

( 2 ) INFORMATION FOR SEQ ID NO:35:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:35:

```
Lys  Lys  Ala  Leu  Lys  Ala  Leu  Lys  Lys  Ala  Leu  Lys  Ala  Leu  Lys  Lys
1                   5                           10                          15

Ala  Leu  Lys  Ala  Leu  Lys  Lys  Ala  Leu  Lys  Ala  Leu
               20                       25
```

( 2 ) INFORMATION FOR SEQ ID NO:36:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear (i i) MOLECULE TYPE: peptide (x i) SEQUENCE DESCRIPTION: SEQ ID NO:36:

Lys Leu Gly Lys Leu Gly Lys
1               5

(2) INFORMATION FOR SEQ ID NO:37:

(i) SEQUENCE CHARACTERISTICS:
        (A) LENGTH: 14 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:37:

Lys Leu Gly Lys Leu Gly Lys Lys Leu Gly Lys Leu Gly Lys
1               5                       10

(2) INFORMATION FOR SEQ ID NO:38:

(i) SEQUENCE CHARACTERISTICS:
        (A) LENGTH: 21 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:38:

Lys Leu Gly Lys Leu Gly Lys Lys Leu Gly Lys Leu Gly Lys Lys Leu
1               5                       10                      15
Gly Lys Leu Gly Lys
                20

(2) INFORMATION FOR SEQ ID NO:39:

(i) SEQUENCE CHARACTERISTICS:
        (A) LENGTH: 28 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:39:

Lys Leu Gly Lys Leu Gly Lys Lys Leu Gly Lys Leu Gly Lys Lys Leu
1               5                       10                      15
Gly Lys Leu Gly Lys Lys Leu Gly Lys Leu Gly Lys
                20                      25

(2) INFORMATION FOR SEQ ID NO:40:

(i) SEQUENCE CHARACTERISTICS:
        (A) LENGTH: 7 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:40:

Lys Lys Leu Gly Lys Leu Gly
1               5

(2) INFORMATION FOR SEQ ID NO:41:

( i ) SEQUENCE CHARACTERISTICS:
   ( A ) LENGTH: 14 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:41:

```
Lys Lys Leu Gly Lys Leu Gly Lys Lys Leu Gly Lys Leu Gly
1               5                   10
```

( 2 ) INFORMATION FOR SEQ ID NO:42:

( i ) SEQUENCE CHARACTERISTICS:
      ( A ) LENGTH: 21 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:42:

```
Lys Lys Leu Gly Lys Leu Gly Lys Lys Leu Gly Lys Leu Gly Lys Lys
1               5                   10                  15

Leu Gly Lys Leu Gly
            20
```

( 2 ) INFORMATION FOR SEQ ID NO:43:

( i ) SEQUENCE CHARACTERISTICS:
      ( A ) LENGTH: 28 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:43:

```
Lys Lys Leu Gly Lys Leu Gly Lys Lys Leu Gly Lys Leu Gly Lys Lys
1               5                   10                  15

Leu Gly Lys Leu Gly Lys Lys Leu Gly Lys Leu Gly
            20                  25
```

( 2 ) INFORMATION FOR SEQ ID NO:44:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:44:

```
Lys Phe Ala Lys Lys Phe Ala
1               5
```

( 2 ) INFORMATION FOR SEQ ID NO:45:

( i ) SEQUENCE CHARACTERISTICS:
      ( A ) LENGTH: 14 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:45:

```
Lys  Phe  Ala  Lys  Lys  Phe  Ala  Lys  Phe  Ala  Lys  Lys  Phe  Ala
1                  5                           10
```

( 2 ) INFORMATION FOR SEQ ID NO:46:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:46:

```
Lys  Phe  Ala  Lys  Lys  Phe  Ala  Lys  Phe  Ala  Lys  Lys  Phe  Ala  Lys  Phe
1                  5                           10                          15

Ala  Lys  Lys  Phe  Ala
                20
```

( 2 ) INFORMATION FOR SEQ ID NO:47:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:47:

```
Lys  Phe  Ala  Lys  Lys  Phe  Ala  Lys  Phe  Ala  Lys  Lys  Phe  Ala  Lys  Phe
1                  5                           10                          15

Ala  Lys  Lys  Phe  Ala  Lys  Phe  Ala  Lys  Lys  Phe  Ala
                20                          25
```

( 2 ) INFORMATION FOR SEQ ID NO:48:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:48:

```
Lys  Lys  Phe  Ala  Lys  Phe  Ala
1                   5
```

( 2 ) INFORMATION FOR SEQ ID NO:49:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:49:

```
Lys  Lys  Phe  Ala  Lys  Phe  Ala  Lys  Lys  Phe  Ala  Lys  Phe  Ala
1                   5                            10
```

( 2 ) INFORMATION FOR SEQ ID NO:50:

( i ) SEQUENCE CHARACTERISTICS:
        ( A ) LENGTH: 21 amino acids
        ( B ) TYPE: amino acid
        ( C ) STRANDEDNESS: single (D) TOPOLOGY: linear (i i) MOLECULE TYPE: peptide (x i) SEQUENCE DESCRIPTION: SEQ ID NO:50:

```
Lys Lys Phe Ala Lys Phe Ala Lys Lys Phe Ala Lys Phe Ala Lys Lys
1               5                   10                  15
Phe Ala Lys Phe Ala
            20
```

(2) INFORMATION FOR SEQ ID NO:51:

(i) SEQUENCE CHARACTERISTICS:
        (A) LENGTH: 28 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:51:

```
Lys Lys Phe Ala Lys Phe Ala Lys Lys Phe Ala Lys Phe Ala Lys Lys
1               5                   10                  15
Phe Ala Lys Phe Ala Lys Lys Phe Ala Lys Phe Ala
            20                  25
```

(2) INFORMATION FOR SEQ ID NO:52:

(i) SEQUENCE CHARACTERISTICS:
        (A) LENGTH: 21 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:52:

```
Leu Ser Leu Xaa Leu Ser Leu Leu Ser Leu Xaa Leu Ser Leu Leu Ser
1               5                   10                  15
Leu Xaa Leu Ser Leu
            20
```

(2) INFORMATION FOR SEQ ID NO:53:

(i) SEQUENCE CHARACTERISTICS:
        (A) LENGTH: 18 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:53:

```
Leu Lys Leu Leu Lys Lys Leu Leu Lys Lys Leu Lys Lys Leu Leu Lys
1               5                   10                  15
Lys Leu
```

(2) INFORMATION FOR SEQ ID NO:54:

(i) SEQUENCE CHARACTERISTICS:
        (A) LENGTH: 21 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:54:

```
Leu Ser Ser Leu Leu Ser Leu Leu Ser Ser Leu Leu Ser Leu Leu Ser
1           5                   10                  15
Ser Leu Leu Ser Leu
        20
```

AMPHIPATHIC PEPTIDES

This application is a continuation of copending application Ser. No. 08/789,077, filed Feb. 3, 1997 now abandoned; which is a continuation of application Ser. No. 08/681,075, filed Jul. 22, 1996, now abandoned; which is a continuation of application Ser. No. 08/232,525, filed Apr. 22, 1994, now abandoned.

The development of this invention was partially funded by the Government under grant NSF/LEQSF(1992–96)-ADP-01 awarded by the National Science Foundation. The Government may have certain rights in this invention.

Lytic peptides, also known as channel-forming peptides, are broad spectrum antibacterial agents. The peptides typically disrupt cell membranes, causing cell lysis and death. The specificity of various lytic peptides can differ. For example, melittin, a component of honey bee venom, is not selective. The minimum bactericidal concentration of melittin also damages normal mammalian cells. By contrast, the naturally occurring magainins and cecropins exhibit substantial bactericidal activity at concentrations that are not lethal to normal mammalian cells. Synthetic analogs of several naturally occurring lytic peptides have previously been synthesized, but in the past it has been laborious and expensive to synthesize these synthetic peptides in large quantities. There is a continuing need for synthetic lytic peptides that are easy to synthesize, and that exhibit antibacterial activity at concentrations that are not lethal to normal mammalian cells.

Lytic peptides generally have random coil conformations in dilute aqueous solutions. However, high levels of helicity can be induced by helix-promoting solvents and amphipathic media such as micelles, synthetic bilayers, and cell membranes. When helicity is induced, the polar and nonpolar amino acid residues are aligned into an amphipathic helix. (An amphipathic peptide or protein is one in which the hydrophobic amino acid residues are predominantly on one side, while the hydrophilic amino acid residues are predominantly on the opposite side, resulting in a peptide or protein which is predominantly hydrophobic on one face, and predominantly hydrophilic on the opposite face.) In an amphipathic α-helix, the polar and nonpolar amino acid residues are organized into mostly polar and mostly nonpolar faces of the peptide when the peptide is viewed along the helical axis. The polar face of a lytic peptide often has several positively charged residues at physiological pH, while a variety of nonpolar residues can form the nonpolar face.

Nonspecific peptide-membrane interactions apparently suffice to cause cell lytic activity. Sequence homology per se to a native peptide may not be a prerequisite for a synthetic lytic peptide to have biological activity, so long as the peptide remains amphipathic and has a minimum length of about 12–14 amino acid residues. For example, all D-amino acid analogs of melittin, magainin, and cecropin have been reported to have biological activities essentially the same as those of the native peptides. Similarly, simplified analogs of natural peptides that retain or enhance amphipathicity have been shown to be active lytic peptides. Synthetic "minimalist" peptides that are amphipathic in α-helical conformations have been synthesized using combinations of one polar residue and one nonpolar residue. The two key elements for a wide variety of lytic peptides appear to be: (1) a propensity for the peptide to form an amphipathic helix; and (2) a minimum peptide length. While natural lytic peptides are generally greater than 20 amino acid residues in length, synthetic lytic peptides can be biologically active at the much shorter lengths of 12–18 residues. While a great many amino acid sequences can potentially give rise to amphipathic α-helices, it is considerably more difficult to predict a priori which peptides will exhibit selectivity in their lytic properties against living cells.

An initial interaction between the peptide and the cell membrane surface probably orchestrates or stabilizes a coil-helix transition, with polar groups aligning along one face of the peptide, parallel to the membrane surface. The hydrophobic face of the peptide then inserts into the lipid bilayer, while remaining parallel to the surface. Thus the polar face of the peptide is exposed to both the polar head groups of the bilayer and to the external aqueous environment. Three possible mechanisms have been proposed for what happens next in lytic peptide-based cell killing:

(1) The so-called "raft model" suggests that the peptides aggregate in sufficient numbers to disrupt the cell membrane, causing a loss of osmotic integrity and cell killing.

(2) The "channel model" starts with the raft model, and additionally suggests that aggregates containing four to six peptides each form transmembrane channels, where the polar faces of the peptides line the channel and the nonpolar faces of the peptide-aggregate interact with the nonpolar region of the lipid bilayer, thus allowing ions to pass through the cell membrane. If the persistence and numbers of these channels are sufficiently high, a loss of cell osmotic integrity and cell lysis results. A special case of the channel model has been established for gramicidin D, which forms a peptide dimer. But the mechanism of cell killing by other lytic peptides is still in dispute. The composition of the interior surface of the channel formed by the transmembrane peptides can create selectivity for the ions that can pass the channel. For example, the 21-residue synthetic peptides (LSSLLSL)$_3$ (SEQ ID NO. 54) and (LSLXLSL)$_3$ (SEQ ID NO. 52) form cation- and proton-selective channels, respectively.

(3) The "pore model" hypothesizes a larger channel formed from ten or more transmembrane peptides, which would assemble in the same way as in the channel model, except that the polar cavity would be large enough to allow the rapid and unselective passage of fully hydrated ions, thereby destroying the osmotic integrity of the cell.

L. A. Chung et al., "Fluorescence Studies of the Secondary Structure and Orientation of a Model Ion Channel Peptide in Phospholipid Vesicles," Biochemistry, vol. 31, pp. 6608–6616 (1992) discloses that the 21-residue peptide (LSSLLSL)$_3$ (SEQ ID NO. 54) forms ion channels when it is incorporated into planar bilayer membranes of diphytanoylphosphatidylcholine.

N. E. Zhou et al., "Synthetic Model Proteins: The Relative Contribution of Leucine Residues at the Nonequivalent Positions of the 3–4 Hydrophobic Repeat to the Stability of the Two-Stranded α-Helical Coiled-Coil," Biochemistry, vol. 31, pp. 5739–5746 (1992) discusses the relative contribution of leucine residues at different positions to the stability of a two-stranded α-helical coiled coil.

E. K. O'Shea et al., "X-ray Structure of the GCN4 Leucine Zipper, a Two-Stranded, Parallel Coiled Coil," Science, vol. 254, pp. 539–544 (1991) reports that the structure of GCN4, a transcriptional activator for amino acid biosynthesis in yeast, includes a leucine zipper that promotes protein dimer formation.

S. E. Blondelle et al., "Design of Model Amphipathic Peptides Having Potent Antimicrobial Activities," Biochemistry, vol. 31, pp. 12688–12694 (1992) reports that the sequence LKLLKKLLKKLKKLLKKL (SEQ ID NO. 53) adopts an α-helical conformation, and that the peptide has activity against both Gram-positive and Gram-negative bacteria. The activities of certain analogs having various substitutions, omissions, and lengths are also discussed.

W. F. DeGrado et al., "Conformationally Constrained α-Helical Peptide Models for Protein Ion Channels," Biopolymers, vol. 29, pp. 205–213 (1990) discusses amphiphilic α-helical models for ion channels formed from various peptides composed of only Leu and Ser residues, or a modification of such a peptide incorporating α-aminoisobutyric acid.

We have invented novel "minimalist" lytic peptides that may be readily synthesized on a large scale via a highly-convergent, solution-phase synthesis. While other "minimalist" lytic peptides with repetitive sequences have previously been shown to be biologically active, to the knowledge of the inventors no such prior peptides are suitable for convergent synthesis.

The novel peptides are amphipathic, and are easy and inexpensive to synthesize via solution phase techniques. The novel peptides exhibit anti-bacterial properties at concentrations that are not lethal to normal mammalian cells.

Figure 1A:
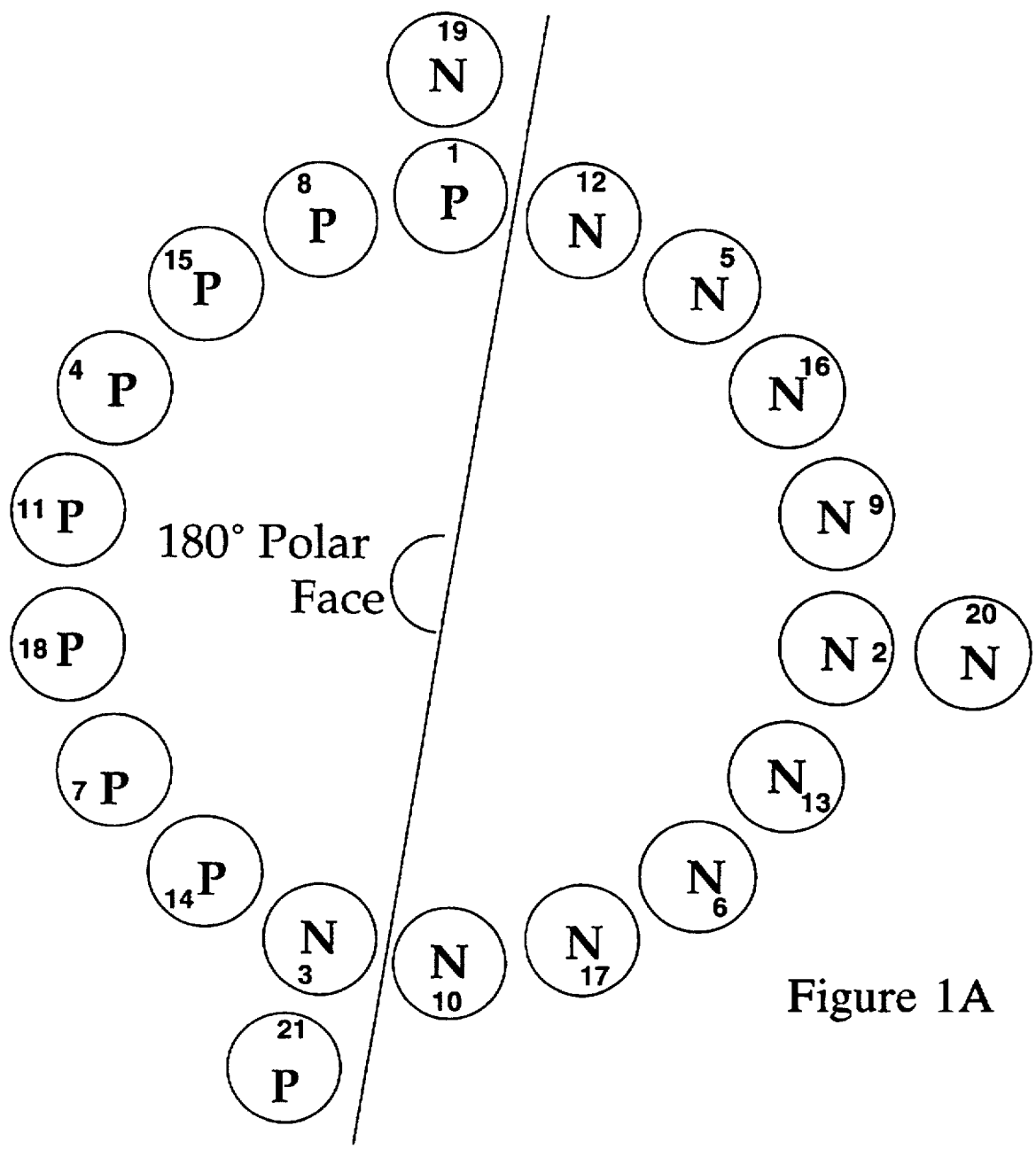
FIG. 1A and 1B illustrate Schiffer-Edmundson wheel diagrams of the general formulas of two 21-mers in accordance with the present invention.

The novel peptides of the present invention comprise multimers, i.e. two or more adjacent repeats, of certain heptads of amino acid residues. The heptads were designed to generate amphipathic peptides when the heptads are combined into multimers, and were further designed to be readily suited for convergent, solution-phase synthesis.

The preferred heptads are described generically by one of the following four formulas, in which "Xps" denotes a positively charged amino acid at physiological pH, and in which "Xnp" denotes a nonpolar amino acid at physiological pH (Xnp may also be glycine, even though glycine is slightly polar): (1) Xps$_1$Xnp$_1$Xnp$_2$Xps$_1$Xnp$_1$Xnp$_2$Xps, or (2) XpsXnp$_1$Xnp$_2$Xps$_1$Xnp$_1$Xnp$_2$Xps$_1$, or (3) Xps$_1$Xnp$_1$Xnp$_2$XpsXps$_1$Xnp$_1$Xnp$_2$, or (4) XpsXps$_1$Xnp$_1$Xnp2Xps$_1$Xnp$_1$Xnp$_2$.

Other heptads that are also expected to work in the present invention include those of the following formulas: (5) Xnp$_1$Xnp$_2$Xps$_1$Xnp$_1$Xnp$_2$Xps$_1$Xps, or (6) Xnp$_1$Xnp$_2$Xps$_1$XpsXnp$_1$Xnp$_2$Xps$_1$; or (7) Xnp$_1$Xps$_1$Xps$_2$Xnp$_1$Xps$_1$Xps$_2$Xnp, or (8) XnpXps$_1$Xps$_2$Xnp$_1$Xps$_1$Xps$_2$Xnp$_1$, or (9) XnpXnp$_1$Xps$_1$Xps$_2$Xnp$_1$Xps$_1$Xps$_2$, or (10) Xps$_1$Xps$_2$Xnp$_1$Xps$_1$Xps$_2$Xnp$_1$Xnp, or (11) Xps$_1$Xps$_2$Xnp$_1$XnpXps$_1$Xps$_2$Xnp$_1$or (12) Xnp$_1$Xps$_1$Xps$_2$XnpXnp$_1$Xps$_1$Xps$_2$; or (13) Xnp$_1$Xnp$_2$Xps$_1$Xnp$_1$Xnp$_2$Xps$_1$Xnp, or (14) XnpXnp$_1$Xnp$_2$Xps$_1$Xnp$_1$Xnp$_2$Xps$_1$, or (15) Xps$_1$Xnp$_1$Xnp$_2$XnpXps$_1$Xnp$_1$Xnp$_2$, or (16) Xnp$_1$Xps1 Xnp$_2$XnpXnp$_1$Xps$_1$Xnp$_2$, or (17) Xnp$_1$Xnp$_2$Xps$_1$XnpXnp$_1$Xnp$_2$Xps$_1$ or (18) Xps$_1$Xnp$_1$Xnp$_2$Xps$_1$Xnp$_1$Xnp$_2$Xnp, or (19) Xnp$_1$Xps$_1$Xnp$_2$Xnp$_1$Xps$_1$Xnp$_2$Xnp, or (20) XnpXnp$_1$Xps$_1$Xnp$_2$Xnp$_1$Xps$_1$Xnp$_2$, or (21) XnpXps$_1$Xnp$_1$Xnp$_2$Xps$_1$Xnp$_1$Xnp$_2$.

Within a given one of the above formulas, residues of the same type having the same subscript are residues of the same amino acid; e.g., two Xps$_1$ residues in the same formula designate residues of the same positively charged amino acid. Residues of the same type having different subscripts are not necessarily the same, although they may be the same; e.g., an Xnp$_1$ and an Xnp$_2$ residue in the same formula both designate nonpolar amino acid residues, which may or may not be residues of the same amino acid. Within a given formula, two residues of the same type, one of which has a subscript and one of which has no subscript, may or may not be residues of the same amino acid; e.g., an Xnp residue and an Xnp$_1$ residue may or may not designate residues of the same nonpolar amino acid.

The common features of each of the above nineteen general formulas are the following: (1) Each of the formulas designates a heptad. (2) Each of the heptads preferably comprises four nonpolar amino acid residues and three positively charged amino acid residues; or alternatively comprises five nonpolar amino acid residues and two positively charged amino acid residues; or less preferably comprises three nonpolar amino acid residues and four positively charged amino acid residues. (Heptads with three positively charged residues are preferred. Heptads with four positively charged residues, while a possible alternative, are not preferred, because the polar face of the peptide will probably be too large for the peptide to have the desired biological activity. Heptads with two positively charged residues are intermediate in order of preference.) (3) The distribution of the nonpolar residues and positively charged residues within the heptad is such that when multimers of the heptad form an α-helix, the nonpolar residues will lie on one face of the α-helix, and the positively charged residues will lie on the opposite face of the α-helix, thereby promoting amphipathicity. (4) The heptad comprises two repeating triads and one additional residue, so that the heptad has the form (triad)(triad)(residue) or (triad)(residue)(triad) or (residue) (triad) (triad). Each of the triads comprises two nonpolar residues and one positively charged residue, or two positively charged residues and one nonpolar residue. The repeating triads assist in the convergent synthesis of the heptad, and therefore of a multimer formed from the heptad.

Figure 1B:
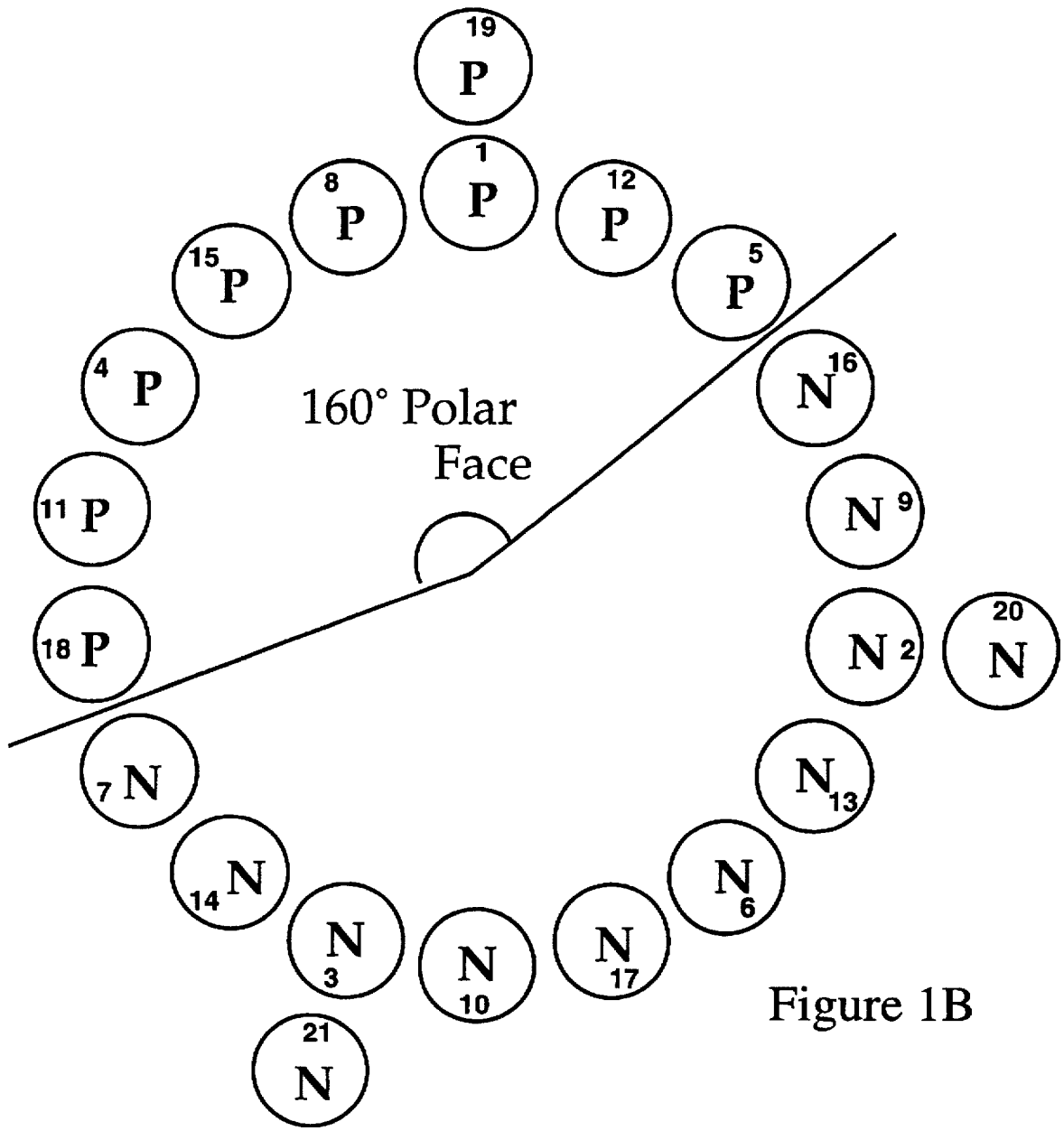

As used in the specification and the claims, a "multimer" of a heptad is a peptide containing two or more adjacent repeats of the same heptad, so that the repeating sequence as a whole contains 14, 21, 28, or possibly a higher multiple of 7 residues: (heptad) (heptad), or (heptad) (heptad) (heptad), or (heptad) (heptad) (heptad) (heptad), etc. A peptide "comprising" such a multimer could optionally include additional residues on either the carboxy terminus or the amino terminus of the multimer as a whole; thus, for example, the following 23-residue sequence would be considered a peptide "comprising" such a multimer: Leu(heptad)(heptad)(heptad)Lys. 21-mers containing three heptads of the first and third of the above general formulas are illustrated as Edmundson wheel diagrams in FIGS. 1A and 1B, respectively. (For the sake of brevity, in FIGS. 1A and 1B, P rather than Xps is used to denote a positive residue, and N rather than Xnp is used to denote a nonpolar residue.) Note the polar and nonpolar faces shown in FIGS. 1A and 1B.

Although the peptides of this invention are not limited to the "natural" amino acids used in naturally occurring proteins,or economic reasons it will often be preferable to make the peptides from those "natural" amino acids. In such a case, Xps could be lysine, arginine, or histidine. Lysine is preferred for Xps because it is easy to couple; also, peptides containing lysine may be more biologically active. Each Xps in a given heptad is preferably the same, to simplify the convergent synthesis.

Similarly, where "natural" amino acids are used, Xnp could be alanine, valine, leucine, isoleucine, proline, tryptophan, phenylalanine, or methionine. Xnp may also be glycine, even though glycine is slightly polar. (For purposes of simplicity of terminology, as used in the specification and claims glycine will be considered to be a "nonpolar amino acid.") Combinations of alanine, leucine, phenylalanine, and glycine are preferred for the Xnp's. Leucine and phenylalanine are relatively easy to incorporate, and promote the formation of α-helices. Glycine is relatively easy to incorporate, but does not promote the formation of α-helices. However, glycine is useful for peptide fragment coupling; because glycine is not chiral, racemization of glycine is not a concern. Alanine is not as nonpolar, but it does promote the formation of α-helices.

Alternatively, xenobiotic (or "non-natural") amino acid residues known in the art and otherwise satisfying the criteria for the amino acid residues used in this invention may also be used in the synthesis of peptides in accordance with the present invention. For example, the total or partial replacement of natural L-amino acid residues with the corresponding D-amino acid residues could have advantages when the peptides are used as drugs, because D-amino acid peptides are not readily metabolized. As was discussed above, D-amino acid amphipathic peptides exhibit substantially the same anti-bacterial properties as do the corresponding L-amino acid peptides. Substitution of D-amino acids in the peptides could be total or partial. Without wishing to be bound by this theory, it is expected that one D-amino acid residue per heptad, or one D-amino acid residue per triad should, in general, suffice to protect the peptide from being metabolized. It is intended that where a specific amino acid residue is recited in a claim element below, that the claim element should be construed to encompass both the L-form and the D-form of that amino acid residue. It is intended that where a generic type of amino acid residue is recited in a claim element below (e.g., "positively charged amino acid residue" or "nonpolar amino acid residue"), that the claim element should be construed to cover both a natural amino acid residue as described, and a xenobiotic amino acid residue as described, including (but not limited to) the D-form of a natural amino acid residue.

Preferred peptides within the scope of the present invention include the following:

(KLAKKLA), (KLAKKLA)$_2$, (KLAKKLA)$_3$, (KLAKKLA)$_4$;
(KLAKLAK), (KLAKLAK)$_2$, (KLAKLAK)$_3$, (KLAKLAK)$_4$;
(KKLAKLA), (KKLAKLA)$_2$, (KKLAKLA)$_3$, (KKLAKLA)$_4$;
(KALKKAL), (KALKKAL)$_2$, (KALKKAL)$_3$, (KALKKAL)$_4$;
(KALKALK), (KALKALK)$_2$, (KALKALK)$_3$, (KALKALK)$_4$;
(KKALKAL), (KKALKAL)$_2$, (KKALKAL)$_3$, (KKALKAL)$_4$;
(KLGKKLG), (KLGKKLG)$_2$, (KLGKKLG)$_3$, (KLGKKLG)$_4$;
(KLGKLGK), (KLGKLGK)$_2$, (KLGKLGK)$_3$, (KLGKLGK)$_4$;
(KKLGKLG), (KKLGKLG)$_2$, (KKLGKLG)$_3$, (KKLGKLG)$_4$;
(KFAKKFA), (KFAKKFA)$_2$, (KFAKKFA)$_3$, (KFAKKFA)$_4$;
(KFAKFAK), (KFAKFAK)$_2$, (KFAKFAK)$_3$, (KFAKFAK)$_4$;
(KKFAKFA), (KKFAKFA)$_2$, (KKFAKFA)$_3$, (KKFAKFA)$_4$ (i.e., SEQ ID NO's 1–12, 15–22, 24–51).

Figure 2:
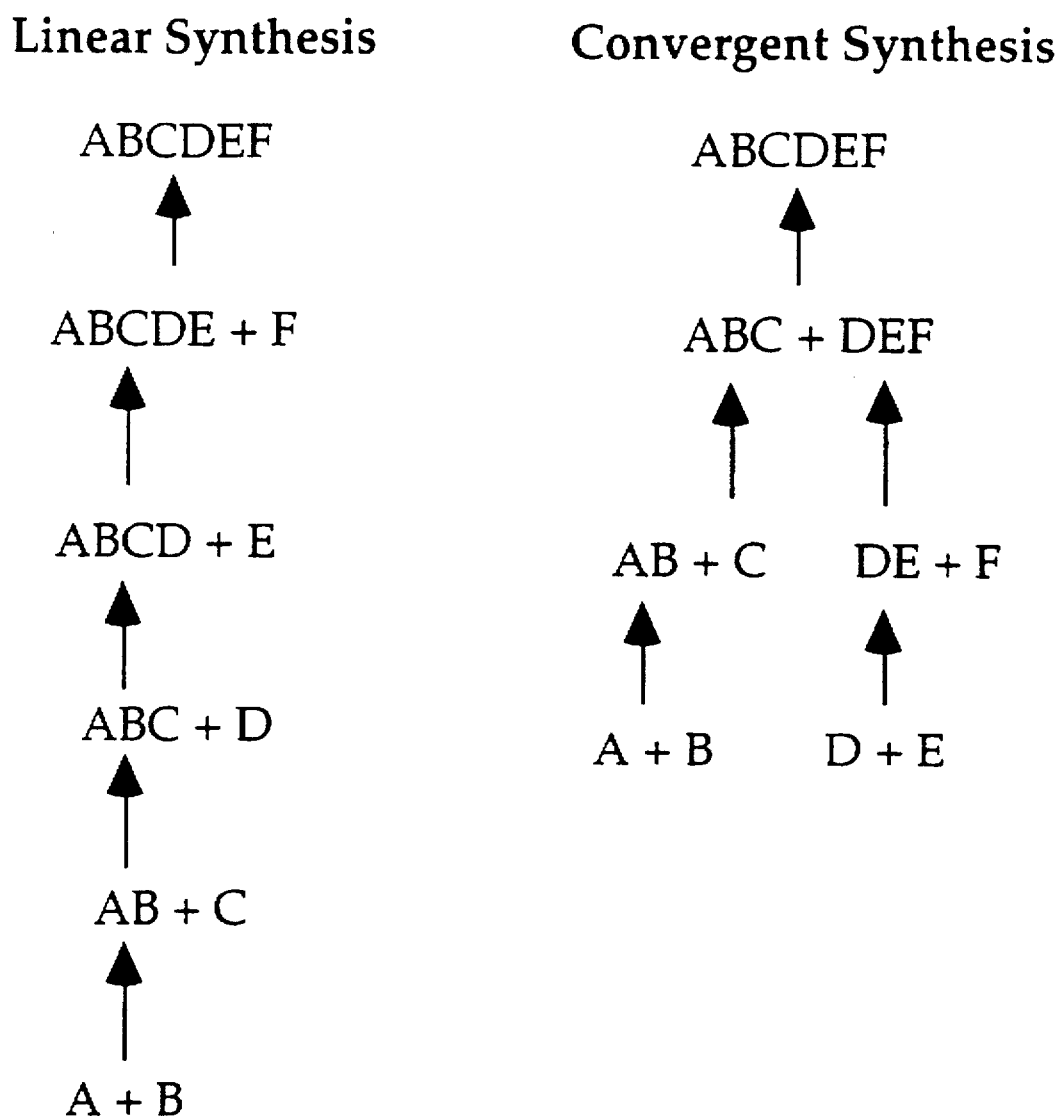
FIG. 2 illustrates schematically the general principal behind a convergent synthetic scheme, versus a linear synthetic scheme.

As one example of a novel peptide in accordance with the present invention, we have discovered that the novel peptide (KLAKKLA)$_2$-OCH$_3$ (SEQ ID NO. 2) selectively lyses representative Gram-negative and Gram-positive bacteria at concentrations that are not lytic to mammalian cells. Linear synthesis of a 14-mer peptide on a solid phase resin involves 30 steps, an initial amino acid-resin coupling step, 14 deprotection and coupling steps, and a final deprotection step, whereas our convergent, solution-phase synthetic approach to (KLAKKLA)$_2$-OCH$_3$(SEQ ID NO. 2) may be completed in only 14 steps. This convergent approach takes advantage of the repetitive nature of the heptads, and of repetition within the heptad itself. The general principal behind a convergent synthetic scheme, versus a linear synthetic scheme, is illustrated schematically in FIG. 2.

Figure 3:
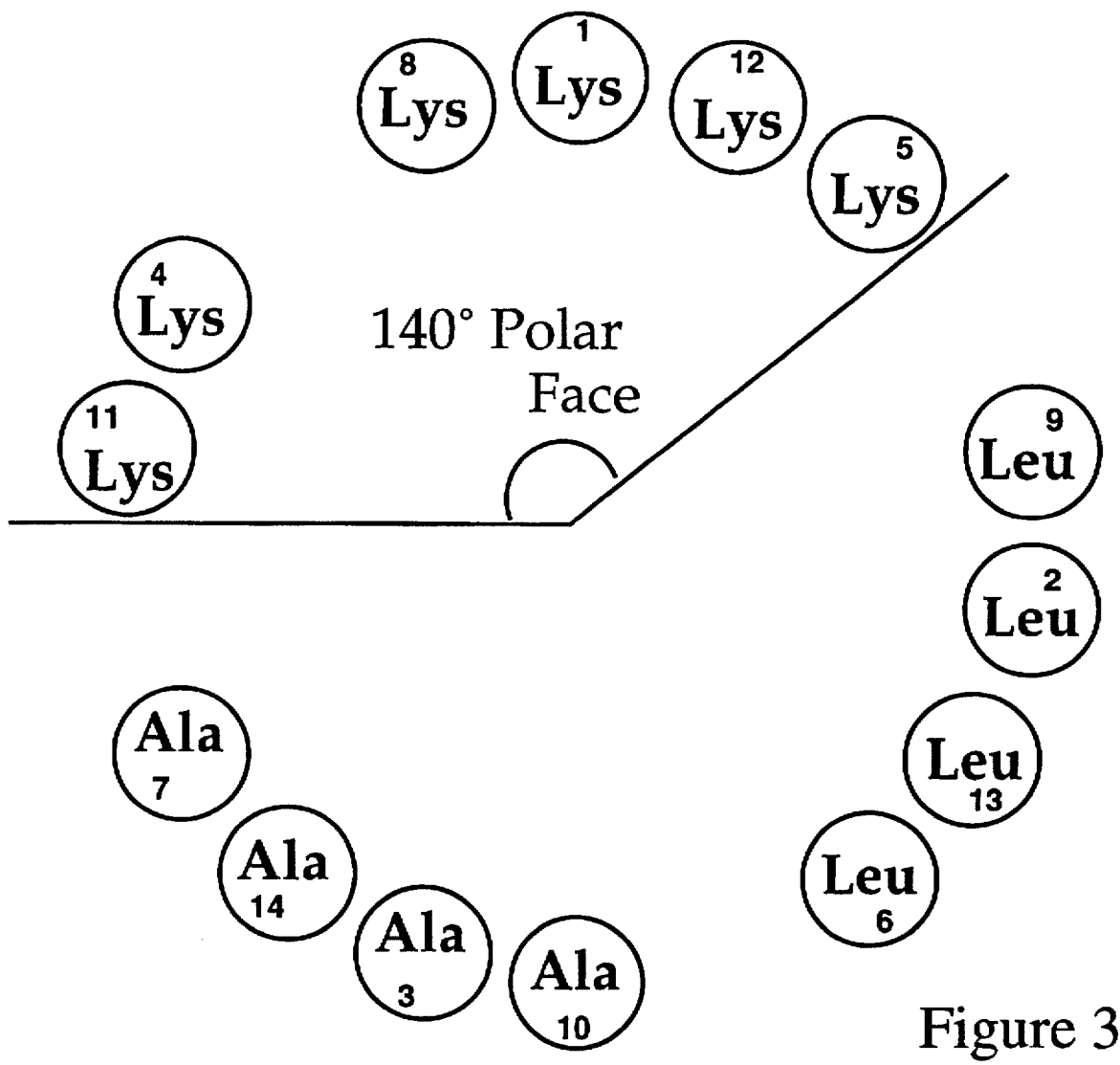
FIG. 3 illustrates a Schiffer-Edmundson helical wheel of (KLAKKLA)$_2$ (SEQ ID NO. 2).

A heptad unit in an α-helix is nearly two revolutions around the helical axis. Repetition of a heptad in an α-helix will automatically keep the same amino acid residues lined up on the same face of the helix when viewed along the helical axis. Residues within a heptad unit that are 3 or 4 residues apart are also proximate in an α-helix. FIG. 3, a Schiffer-Edmundson helical wheel of (KLAKKLA)$_2$ (SEQ ID NO. 2), illustrates the high level of amphipathicity of this peptide. (Schiffer-Edmundson wheels for the other peptides disclosed in this specification are not shown, but may readily be generated by following this example. Several such additional illustrations are shown, for example, in the Becker PhD Dissertation, cited below.)

Before embarking on the design of a suitable solution-phase peptide synthesis, we first synthesized several structurally related peptides via automated solid phase peptide synthesis, to ascertain that the desired biological activity would be retained in the novel peptides. After obtaining this confirmation, we proceeded to design a solution-phase synthesis.

Via solid-phase peptide synthesis, a series of highly repetitive amphipathic peptides 7–28 residues long were prepared, comprising lysines with alanines, leucines, glycines, or phenylalanines. Each peptide was formed from repeating heptads, each of which in turn was formed from two repeating triads with one additional residue. With such highly repetitive sequences, the number of steps needed to synthesize the peptides via convergent solution-phase synthesis is significantly shorter than would be the case for linear solid-phase synthesis. Systematically varying the heptad sequence and amino acid content can be used to optimize biological activity, helical propensity, and aggregation characteristics.

Amino acids for the peptide syntheses were purchased from Milligen, Marlborough, Mass. Peptides were stored frozen as lyophilized powders.

Peptide Synthesis (Solid Phase)

The primary structures for the various peptides are listed above. The usual single-letter amino acid code has been used to represent the amino acid residues (i.e., A=Alanine, K=Lysine, L=Leucine, F=Phenylalanine, G=Glysine). The peptides were synthesized on a Milligen 9050 Pepsyn™ automated peptide synthesizer. Two of the peptides, (KLAKLAK)₃ (SEQ ID NO. 7) and (KFAKFAK)₃ (SEQ ID NO. 11), were synthesized on a peptide-amide linker polystyrene resin (PAL-PS) using fluorenylmethyl chloroformate (FMOC) and pentafluorophenyl ester chemistry. Lysines were protected with a tert-butoxycarbonyl group (t-BOC) at the N-6 position. Lysines for peptides 1 and 2 were double-coupled. All other peptides in the series were prepared using a polyethyleneglycol-polyamide linker on a polystyrene resin support.

Each amino acid came in a pre-weighed vial containing 0.792 mmol (a four-fold excess) of the derivatized amino acid. A number of steps were used to couple the amino acids. Initially, a 30 second DMF (dimethylformamide) wash at 5 mL/min washed the resin/peptide, followed by a 10 minute piperidine wash at 5 mL/min to remove the FMOC from the N-terminus. The resin/peptide was again washed with DMF for 12 minutes (at 5 mL/min) to remove all piperidine so that no premature deprotection on the next amino acid occurred.

During this time, the next amino acid was being dissolved in a solution of DMF and 1-hydroxybenzotriazole (HOBT). The injection probe was washed with the DMF/HOBT solution for 15 seconds at 10 mL/min. The amino acid was then sent to the resin for a one-hour acylation period, followed by an eight minute DMF wash to remove excess amino acid. The probe was again washed with the DMF/HOBT solution for one minute at 10 mL/min. The cycle was then repeated for each additional amino acid.

There were two modifications to the above general protocol. First, all adjacent lysine residues were double-coupled. That is, they underwent a second acylation period following the coupling of the first of the two lysines. However, there was no piperidine wash at the beginning of the second cycle. The second modification concerned the final residue, after which there was a second ten-minute piperidine wash at 5 mL/min to remove the FMOC from the final amino acid residue. This final cycle ended with a twelve-minute DMF wash at 5 mL/min, a 15 minute DCM (dichloromethane) wash at 5 mL/min, and a manual wash with methanol for 15 minutes to shrink the resin to facilitate cleavage of the peptide from the resin. The resin/peptide was then filtered and dried. The peptide was cleaved from the resin using reagent R, a solution of 9.0 mL of trifluoroacetic acid, 0.5 mL thioanisol, 0.3 mL ethanedithiol, and 0.2 mL anisole; or using reagent B, a solution of 8.8 mL trifluoroacetic acid, 0.5 mL phenol, 0.5 mL water, and 0.2 mL triisopropyl silane. Argon was bubbled through the cleavage reagent to degas it. The peptide/resin was shaken under argon every thirty minutes for a period of four hours in the case of reagent R, or stirred for two hours in the case of reagent B. By the end of this time, the peptide had been cleaved from the resin, and the mixture was filtered to remove the resin.

The solution was dispensed by drops in equal volumes into six tubes of cold diethyl ether, with 20 mL ether in each tube. A white precipitate of crude peptide formed in each tube. The tubes were then centrifuged for 20 minutes at 7,000 rpm. The ether was discarded, and the peptide was washed with cold ether and centrifuged three additional times, followed by drying under vacuum overnight to leave approximately 500 mg of crude peptide. Several portions of the crude peptide were filtered on Sephadex G-15™ medium (buffer 0.1M acetic acid, 4.5×55 cm column) in approximately 100 mg lots. The collected fractions were dried under vacuum for a period of two days. Semipreparative RP-HPLC (reversed phase-high pressure liquid chromatography) on a Waters™ C₁₈ column with a gradient of 0.05% TFA (trifluoroacetic acid) in water and acetonitrile for all peptides was used to purify the crude peptide—except for (LKLALKL)₃ (SEQ ID NO. 13) and (LKLGLKL)₃LFL (SEQ ID NO. 14), for which a gradient of 0.05% TFA in water and isopropanol was used. Mass spectroscopy was used to verify molecular weights.

Assay Procedure

Minimum inhibitory concentrations of several of the peptides were measured against *E. coli* ATCC 25922, *Pseudomonas aeruginosa* ATCC 27853, and *Staphylococcus aureus* ATCC 25723. Minimum inhibitory concentrations were obtained by the broth microdilution method. Peptide solutions were prepared over a range of concentrations from 2 µg/mL to 256 µg/mL. $5 \times 10^4$ cells were added to the peptide solutions in sterile wells and incubated overnight. Wells in which the organisms grew became turbid. The minimum inhibitory concentration was the lowest concentration that inhibited growth of the organism. Results are shown in Table 1 below.

Also shown in Table 1 are sublethal concentrations for some of the peptides against the murine cell lines 3T3 and 3T12. Dilutions of peptide were prepared over a range of concentrations. Equal volumes of peptide solution and 250–750 murine cells were mixed together. The cells were incubated for thirty minutes at 37° C. 50 µL of Tryptan blue stain were then added to each well. Under light microscopy, killed cells could be visualized by the fact that their nuclei were stained. The sublethal dose was the highest concentration for which at least one cell nucleus was not stained. (Blank entries in Table 1 correspond to assays that had not been completed as of the date this application is being filed. Values for those entries will be determined in future assays performed in the same manner.)

*P. aeruginosa* and *E. coli* are Gram-negative bacteria, while *S. aureus* is a Gram-positive bacterium. 3T3 cells are healthy Swiss mouse fibroblast cells, and 3T12 cells are transformed, immortalized mouse fibroblast cells. Thus the novel peptides (at the proper concentrations) have activity against both Gram-negative and Gram-positive bacteria, while not showing activity against mammalian cells. This combination of properties is itself rather unusual in a lytic peptide.

TABLE 1

Minimum Inhibitory (for bacteria) and Sublethal (for mammalian cells) Concentrations, in µM

| Peptide | E. coli | P. aeruginosa | S. aureus | 3T3 | 3T12 |
|---|---|---|---|---|---|
| (KLAKKLA) (SEQ ID NO. 1) | >100 | >100 | >100 | N.L. | N.L. |
| (KLAKKLA)₂ (SEQ ID NO. 2) | 6.0 | 3.0 | 6.0 | 394 | 788 |
| (KLAKKLA)₃ (SEQ ID NO. 3) | 4.2 | 4.2 | 4.2 | 9 | 17 |
| (KLAKKLA)₄ (SEQ ID NO. 4) | 9.0 | 9.0 | 9.0 | 13 | 52 |
| (KLAKLAK) (SEQ ID NO. 5) | >95 | >95 | >95 | | |
| (KLAKLAK)₂ (SEQ ID NO. 6) | 5.8 | 5.8 | 5.8 | | |
| (KLAKLAK)₃ (SEQ ID NO. 7) | 3.7 | 3.7 | 3.7 | | |
| (KLAKLAK)₄ (SEQ ID NO. 8) | 9.4 | 9.4 | 9.4 | | |
| (KALKALK)₃ (SEQ ID NO. 9) | 3.9 | 3.9 | 7.8 | | |
| (KLGKKLG)₃ (SEQ ID NO. 21) | 3.4 | 3.4 | 3.4 | 565 | 565 |
| magainin 2 | 1.3 | 0.65 | 1.3 | | |
| melittin | 0.56 | 2.3 | 0.56 | 0.78 | 0.78 |
| cecropin B | 0.20 | 0.20 | 1.7 | | |

Thus the peptides have been demonstrated to have antibacterial properties in vitro. Based on prior work by others with other amphipathic peptides in vivo, it is expected that the novel peptides of the present invention will also have antibacterial properties in vivo.

Peptide Synthesis (Solution Phase)

Figure 4:
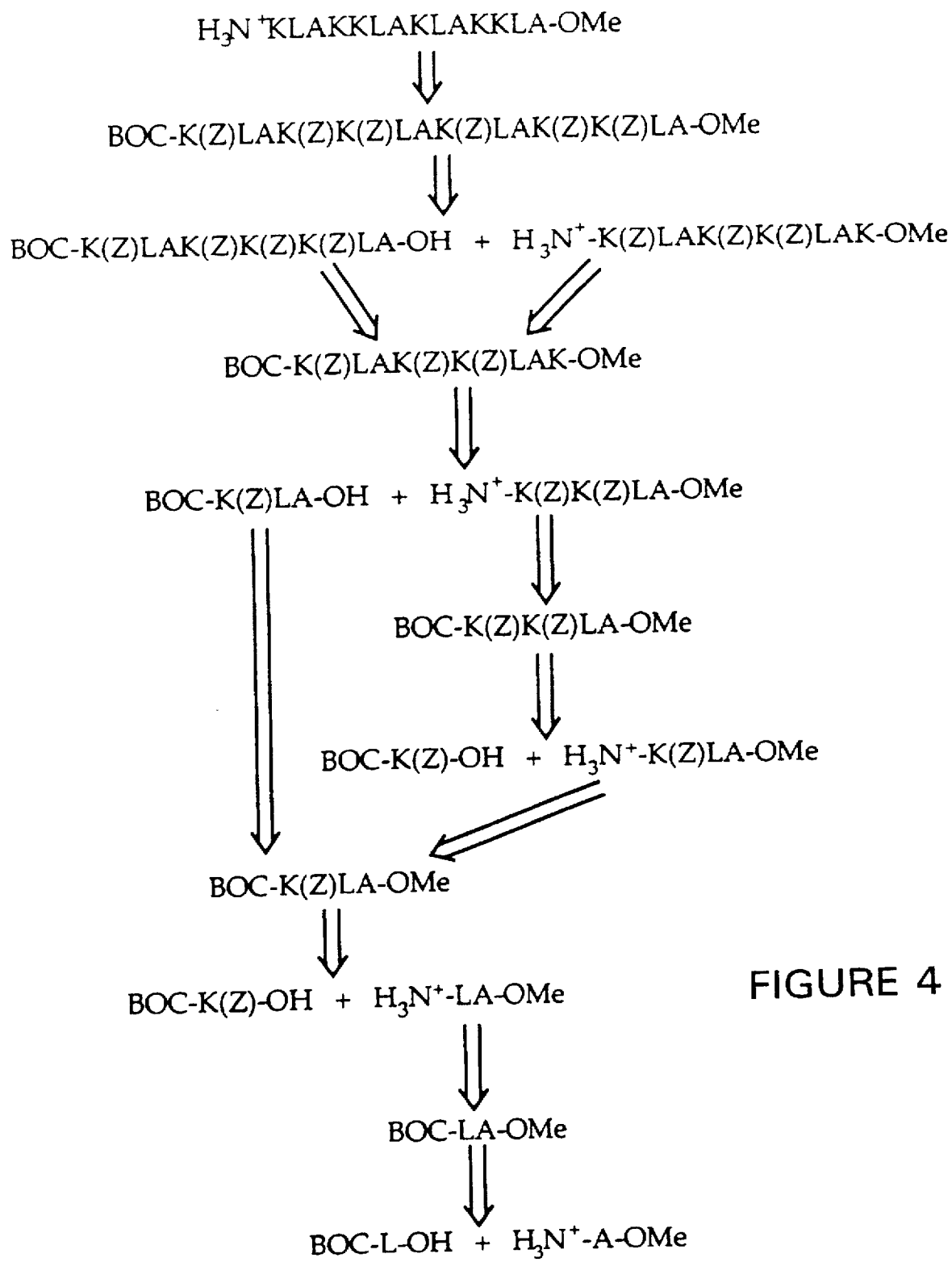
FIG. 4 illustrates a "retrosynthetic analysis" of the 14-mer (KLAKKLA)$_2$-OCH$_3$ (SEQ ID NO. 2).

As an example of the solution phase synthesis of peptides in accordance with the present invention, a detailed description will be given for the synthesis of the 14-mer (KLAKKLA)$_2$-OCH$_3$ (SEQ ID NO. 2). The design of lytic peptides such as this 14-mer allowed a simplified, convergent synthetic approach for a peptide displaying antibacterial activity. The highly repetitive peptide sequence may be built efficiently using peptide fragment couplings. A "retrosynthetic analysis" of the synthesis is depicted in FIG. 4. Racemization during activation and coupling of the C-terminus peptide fragment was not a problem using HOAT (hydroxyazatriazole) as catalyst/additive. The 1–4 hydrophobic amino acid repeats within the heptad helped insure that the peptide was amphipathic, in an $\alpha$-helical conformation. The peptide (KLAKKLA)$_2$-OCH$_3$ (SEQ ID NO. 2) was found to be a broad spectrum antibacterial agent at concentrations that were not lytic to normal mammalian cells in cell culture. See Table 1.

Alanine and leucine are helix-promoting residues in amphipathic helix peptides. Lysine, protected at the epsilon nitrogen as the benzyloxycarbonyl derivative (sometimes designated Z), is the least expensive positively-charged amino acid to couple. Standard t-BOC peptide synthesis, starting from the C-terminus, gives high yields and is generally free of racemization problems. However, C-terminus peptide fragments are susceptible to racemization during coupling. Alanine residues were incorporated at all the C-terminus peptide fragment coupling sites in (KLA-KKLA-)$_2$-OCH$_3$ (SEQ ID NO. 2) to reduce steric hindrance to peptide coupling.

The peptide fragment t-BOC-(Z)KLA-OCH$_3$ was synthesized according to known methods in four steps. A portion of the trimer was extended by deprotection and coupling to give t-BOC-(Z)K(Z)KLA-OCH$_3$ (SEQ ID NO. 23) in good yield. Another portion of the trimer was saponified and coupled to deprotected (Z)K(Z)KLA-OCH$_3$ (SEQ ID NO. 23) to give t-BOC-(Z)KLA(Z)K(Z)KLA-OCH$_3$ (SEQ ID NO. 1) in good yield. The potentially racemized by-product (D)-A$_3$ labeled heptad was specifically synthesized to compare its chromatographic retention with the (L)-heptad. Traces of racemized peptide were detected in the products of the synthesis, and the pure (L)-heptad was readily separated from the diastereomeric peptide and other impurities via flash column chromatography on silica gel by eluting with 10:1 chloroform/methanol. The (L)-heptad was coupled to itself by the same approach as used above to give t-BOC-(Z)KLA(Z)K(Z)KLA(Z)KLA(Z)K(Z)KLA-OCH$_3$ (SEQ ID NO. 2), along with the specifically (D)-A$_7$ labeled 14-mer. The power of this approach is evident in that only three or four more steps are needed to prepare either a 21-mer or a 28-mer, although peptide solubility may become limiting with peptides beyond the 14-mer.

The solubility problem could be overcome, for example, by using Z-group analogs that solubilize the protected peptide fragments. See, e.g., the following paper, the entire disclosure of which is incorporated by reference: A. Zier et al., "Polyethylene Glycol Bound Benzyl- and Fluorenyl Derivatives as Solubilizing Side-Chain Protecting Groups in Peptide Synthesis," Tetrahedron Letters, vol. 35, pp. 1039–1042 (1994).

In marked contrast, linear syntheses of these peptides would take 44 and 58 steps, respectively, and would be plagued by insertion or deletion by-products that differed by only one or a few residue(s). Such by-products do not build up in the solution phase method, because incompletely coupled by-products are removed prior to the next coupling step, and incompletely coupled products that differ by an entire heptad unit are easily removed. Fortunately, the diastereomeric peptides produced in small amounts by racemization during C-terminus peptide fragment coupling may be easily removed using flash column chromatography.

Concomitant deprotection of t-BOC- and Z-groups gave the heptad and 14-mer esters, which were then purified using a 0.05% TFA water/acetonitrile gradient on a semi-preparative C-4 reversed-phase HPLC column. The purified heptad and 14-mer peptides were also well resolved from specifically-synthesized D-alanine labeled peptides, using standard RP-HPLC conditions.

To date, purity rather than yield optimization has been emphasized in the syntheses. Yields have averaged about 80% per step, for an overall yield of approximately 5%. In spite of this relatively low overall yield, a single worker of ordinary skill in the art may use this synthetic approach to prepare several hundreds of milligrams of the (L)-14-mer within three weeks on a laboratory-bench scale.

Plasma desorption mass spectrometry (PD)MS) and amino acid analysis were used to prove the composition of the fully protected peptides. The deprotected peptide was also analyzed via PDMS.

As illustrated in Table 1 above, the antibacterial activity of the 14-mer was comparable to that of various natural lytic peptides, except for melittin, which indiscriminantly lyses both bacterial and mammalian cells. The 14-mer was observed to begin mammalian cell permeation to an exterior fluorescent dye at concentrations about 50 times higher than the concentrations of the 14-mer that effectively inhibited bacterial growth.

Miscellaneous

Any of the peptides taught in this specification may be synthesized through means known in the art with a peptide synthesizer.

By analogy to the convergent synthesis described in this specification, convergent syntheses of other peptides in accordance with the present invention may be carried out by the worker of ordinary skill in the art using known synthetic techniques of peptide and organic chemistry Because peptides in accordance with the present invention are amphipathic, such peptides will have in vitro antibacterial activity. Assays for such activity may be performed as described above. It is expected that many of these peptides will also have in vivo activity. Screening a particular peptide for in vivo activity may be readily carried out by one of ordinary skill in the art.

Lytic peptide biological activity does not appear to correlate strongly with the propensity of the peptides to form helices in aqueous solution, suggesting that coil-helix peptide transitions are orchestrated by interactions with the membrane surface. Without wishing to be bound by this theory, it is believed that the formation of complete or partial "leucine zipper" dimers, dimers formed by the interdigitation of the hydrophobic faces of two peptides, may improve the activity of the peptides. A leucine zipper is formed where leucine residues occur every seventh residue within an $\alpha$-helix. Thus inclusion of leucine residues in the repeating heptad units may improve the activity of the amphipathic peptides. While leucine zipper peptide dimers are "stable" only at peptide lengths of 28 or longer, we believe that shorter peptides with leucine-containing faces have an increased tendency towards aggregation.

Placing phenylalanine residues in the nonpolar face makes the nonpolar face more hydrophobic, and may also act to improve the activity of the peptides.

The entire disclosure of the following, currently unpublished dissertation, which is not prior art to the present invention, is incorporated by reference: C. L. Becker, "The Design, Synthesis and Structure-Function Studies of Highly Repetitive Amphiphilic Antibacterial Peptides and the Synthesis of Benz [f]indene for the Preparation of Novel Metallocenes," Louisiana State University (Baton Rouge) PhD Dissertation (May 1994). The entire disclosures of all other references cited in this specification are also incorporated by reference. In the event of an irresolvable conflict, however, the present specification shall control.

We claim:

1. A process for lysing bacteria in the presence of mammalian cells, wherein lysis of the bacteria occurs preferentially over the lysis of the mammalian cells; said process comprising exposing the bacteria and mammalian cells to a lytic peptide at a concentration that causes lysis of the bacteria preferentially over lysis of the mammalian cells; wherein said lytic peptide comprises a dimer of a heptad of amino acid residues, wherein:

(a) said heptad comprises four nonpolar amino acid residues and three positively charged amino acid residues, or comprises five nonpolar amino acid residues and two positively charged amino acid residues;

(b) said nonpolar amino acid residues and said positively charged amino acid residues are distributed within said heptad such that when said multimer forms an α-helix, said nonpolar amino acid residues will lie on one face of the α-helix, and said positively charged amino acid residues will lie on the opposite face of the α-helix, whereby the multimer is amphipathic;

(c) said heptad comprises two repeating triads of amino acid residues and one additional amino acid residue, whereby said heptad has the form triad-triad-residue or triad-residue-triad or residue-triad-triad; and (d) the sequence of amino acid residues in each of the two said triads is the same, and each said triad comprises two nonpolar amino acid residues and one positively charged amino acid residue.

2. A process as recited in claim 1, wherein said lytic peptide comprises the 14-mer (KLAKKLA)$_2$ (SEQ ID NO. 2).

3. A process as recited in claim 1, wherein said lytic peptide comprises the 14-mer (KLAKLAK)$_2$ (SEQ ID NO. 6).

4. A process as recited in claim 1, wherein said lytic peptide comprises the 14-mer (KKLAKLA)$_2$ (SEQ ID NO. 25).

5. A process as recited in claim 1, wherein said lytic peptide comprises the 14-mer (KALKKAL)$_2$ (SEQ ID NO. 29).

6. A process as recited in claim 1, wherein said lytic peptide comprises the 14-mer (KALKALK)$_2$ (SEQ ID NO. 16).

7. A process as recited in claim 1, wherein said lytic peptide comprises the 14-mer (KKALKAL)$_2$ (SEQ ID NO. 33).

8. A process as recited in claim 1, wherein said lytic peptide comprises the 14-mer (KLGKKLG)$_2$ (SEQ ID NO. 20).

9. A process as recited in claim 1, wherein said lytic peptide comprises the 14-mer (KLGKLGK)$_2$ (SEQ ID NO. 37).

10. A process as recited in claim 1, wherein said lytic peptide comprises the 14-mer (KKLGKLG)$_2$ (SEQ ID NO. 41).

11. A process as recited in claim 1, wherein said lytic peptide comprises the 14-mer (KFAKKFA)$_2$ (SEQ ID NO. 45).

12. A process as recited in claim 1, wherein said lytic peptide comprises the 14-mer (KFAKFAK)$_2$ (SEQ ID NO. 10).

13. A process as recited in claim 1, wherein said lytic peptide comprises the 14-mer (KKFAKFA)$_2$ (SEQ ID NO. 49).

14. A process as recited in claim 1, wherein said heptad has a sequence of the form $Xps_1Xnp_1Xnp_2Xps_1Xnp_1Xnp_1Xps$; wherein Xps denotes a positively charged amino acid residue at physiological pH; wherein $Xps_1$ denotes a positively charged amino acid residue at physiological pH, and the two $Xps_1$ residues are residues of the same amino acid; wherein Xps and $Xps_1$ may be the same or different; wherein $Xnp_1$ denotes a nonpolar amino acid residue at physiological pH, and the two $Xnp_1$ residues are residues of the same amino acid; wherein $Xnp_2$ denotes a nonpolar amino acid residue at physiological pH, and the two $Xnp_2$ residues are residues of the same amino acid; and wherein $Xnp_1$ and $Xnp_2$ may be the same or different.

15. A process as recited in claim 1, wherein said heptad has a sequence of the form $XpsXnp_1Xnp_2Xps_1Xnp_1Xnp_2Xps_1$; wherein Xps denotes a positively charged amino acid residue at physiological pH; wherein $Xps_1$ denotes a positively charged amino acid residue at physiological pH, and the two $Xps_1$ residues are residues of the same amino acid; wherein Xps and $Xps_1$ may be the same or different; wherein $Xnp_1$ denotes a nonpolar amino acid residue at physiological pH, and the two $Xnp_1$ residues are residues of the same amino acid; wherein $Xnp_2$ denotes a nonpolar amino acid residue at physiological pH, and the two $Xnp_2$ residues are residues of the same amino acid; and wherein $Xnp_1$ and $Xnp_2$ may be the same or different.

16. A process as recited in claim 1, wherein said heptad has a sequence of the form $Xps_1Xnp_1Xnp_2XpsXps_1Xnp_1Xnp_2$; wherein Xps denotes a positively charged amino acid residue at physiological pH; wherein $Xps_1$ denotes a positively charged amino acid residue at physiological pH, and the two $Xps_1$ residues are residues of the same amino acid; wherein Xps and $Xps_1$ may be the same or different; wherein $Xnp_1$ denotes a nonpolar amino acid residue at physiological pH, and the two $Xnp_1$ residues are residues of the same amino acid; wherein $Xnp_2$ denotes a nonpolar amino acid residue at physiological pH, and the two $Xnp_2$ residues are residues of the same amino acid; and wherein $Xnp_1$ and $Xnp_2$ may be the same or different.

17. A process as recited in claim 1, wherein said heptad has a sequence of the form $XpsXps_1Xnp_1Xnp_2Xps_1Xnp_1Xnp_2$; wherein Xps denotes a positively charged amino acid residue at physiological pH; wherein $Xps_1$ denotes a positively charged amino acid residue at physiological pH, and the two $Xps_1$ residues are residues of the same amino acid; wherein Xps and $Xps_1$ may be the same or different; wherein $Xnp_1$ denotes a nonpolar amino acid residue at physiological pH, and the two $Xnp_1$ residues are residues of the same amino acid; wherein $Xnp_2$ denotes a nonpolar amino acid residue at physiological pH, and the two $Xnp_2$ residues are residues of the same amino acid; and wherein $Xnp_1$ and $Xnp_2$ may be the same or different.

18. A process as recited in claim 1, wherein said heptad has a sequence of the form $Xnp_1Xnp_2Xps_1xnp_1Xnp_2Xps_1Xps$; wherein Xps denotes a positively charged amino acid residue at physiological pH; wherein $Xps_1$ denotes a positively charged amino acid residue at physiological pH, and the two $Xps_1$ residues are residues of the same amino acid; wherein Xps and Xpsmay be the same or different; wherein $Xnp_1$ denotes a nonpolar amino acid residue at physiological pH, and the two $Xnp_1$ residues are residues of the same amino acid; wherein $Xnp_2$ denotes a nonpolar amino acid residue at physiological pH, and the two $Xnp_2$ residues are residues of the same amino acid; and wherein $Xnp_1$ and $Xnp_2$ may be the same or different.

19. A process as recited in claim 1, wherein said heptad has a sequence of the form $Xnp_1Xnp_2Xps_1XpsXnp_1Xnp_2Xps_1$; wherein Xps denotes a positively charged amino acid residue at physiological pH; wherein $Xps_1$ denotes a positively charged amino acid residue at physiological pH, and the two $Xps_1$ residues are residues of the same amino acid; wherein Xps and $Xps_1$ may be the same or different; wherein $Xnp_1$ denotes a nonpolar amino acid residue at physiological pH, and the two $Xnp_1$ residues are residues of the same amino acid; wherein $xnp_2$ denotes a nonpolar amino acid residue at physiological pH, and the two $Xnp_2$ residues are residues of the same amino acid; and wherein $Xnp_1$ and $Xnp_2$ may be the same or different.

20. A process as recited in claim 1, wherein said heptad has a sequence of the form $Xnp_1Xnp_2Xps_1Xnp_1Xnp_2Xps_1Xnp$; wherein each $Xps_1$ denotes a positively charged amino acid residue at physiological pH, and the two $Xps_1$ residues are residues of the same amino acid; wherein Xnp denotes a nonpolar amino acid residue at physiological pH; wherein $Xnp_1$ denotes a nonpolar amino acid residue at physiological pH, and the two $Xnp_1$ residues are residues of the same amino acid; wherein $Xnp_2$ denotes a nonpolar amino acid residue at physiological pH, and the two $Xnp_2$ residues are residues of the same amino acid; and wherein Xnp, $Xnp_1$, and $Xnp_2$ may be the same or different.

21. A process as recited in claim 1, wherein said heptad has a sequence of the form $XnpXnp_1Xnp_2Xps_1Xnp_1Xnp_2Xps_1$; wherein each $Xps_1$ denotes a positively charged amino acid residue at physiological pH, and the two $Xps_1$ residues are residues of the same amino acid; wherein $Xnp_1$ denotes a nonpolar amino acid residue at physiological pH, and the two $Xnp_1$ residues are residues of the same amino acid; wherein $Xnp_2$ denotes a nonpolar amino acid residue at physiological pH, and the two $Xnp_2$ residues are residues of the same amino acid; and wherein $Xnp_1$ and $Xnp_2$ may be the same or different.

22. A process as recited in claim 1, wherein said heptad has a sequence of the form $Xps_1Xnp_1Xnp_2XnpXps_1Xnp_1Xnp_2$; wherein each $Xps_1$ denotes a positively charged amino acid residue at physiological pH, and the two $Xps_1$ residues are residues of the same amino acid; wherein $Xnp_1$ denotes a nonpolar amino acid residue at physiological pH, and the two $Xnp_1$ residues are residues of the same amino acid; wherein $Xnp_2$ denotes a nonpolar amino acid residue at physiological pH, and the two $Xnp_2$ residues are residues of the same amino acid; and wherein $Xnp_1$ and $Xnp_2$ may be the same or different.

23. A process as recited in claim 1, wherein said heptad has a sequence of the form $Xnp_1Xps_1Xnp_2XnpXnp_1Xps_1Xnp_2$; wherein each $Xps_1$ denotes a positively charged amino acid residue at physiological pH, and the two $Xps_1$ residues are residues of the same amino acid; wherein $Xnp_1$ denotes a nonpolar amino acid residue at physiological pH, and the two $Xnp_1$ residues are residues of the same amino acid; wherein $Xnp_2$ denotes a nonpolar amino acid residue at physiological pH, and the two $Xnp_2$ residues are residues of the same amino acid; and wherein $Xnp_1$ and $Xnp_2$ may be the same or different.

24. A process as recited in claim 1, wherein said heptad has a sequence of the form $Xnp_1Xnp_2Xps_1XnpXnp_1Xnp_2Xps_1$; wherein each $Xps_1$ denotes a positively charged amino acid residue at physiological pH, and the two $Xps_1$ residues are residues of the same amino acid; wherein $Xnp_1$ denotes a nonpolar amino acid residue at physiological pH, and the two $Xnp_1$ residues are residues of the same amino acid; wherein $Xnp_2$ denotes a nonpolar amino acid residue at physiological pH, and the two $Xnp_2$ residues are residues of the same amino acid; and wherein $Xnp_1$ and $Xnp_2$ may be the same or different.

25. A process as recited in claim 1, wherein said heptad has a sequence of the form $Xps_1Xnp_1Xnp_2Xps_1Xnp_1Xnp_2Xnp$; wherein each $Xps_1$ denotes a positively charged amino acid residue at physiological pH, and the two $Xps_1$ residues are residues of the same amino acid; wherein $Xnp_1$ denotes a nonpolar amino acid residue at physiological pH, and the two $Xnp_1$ residues are residues of the same amino acid; wherein $Xnp_2$ denotes a nonpolar amino acid residue at physiological pH, and the two $Xnp_2$ residues are residues of the same amino acid; and wherein $Xnp_1$ and $Xnp_2$ may be the same or different.

26. A process as recited in claim 1, wherein said heptad has a sequence of the form $Xnp_1Xps_1Xnp_2Xnp_1Xps_1Xnp_2Xnp$; wherein each $Xps_1$ denotes a positively charged amino acid residue at physiological pH, and the two $Xps_1$ residues are residues of the same amino acid; wherein $Xnp_1$ denotes a nonpolar amino acid residue at physiological pH, and the two $Xnp_1$ residues are residues of the same amino acid; wherein $Xnp_2$ denotes a nonpolar amino acid residue at physiological pH, and the two $Xnp_2$ residues are residues of the same amino acid; and wherein $Xnp_1$ and $Xnp_2$ may be the same or different.

27. A process as recited in claim 1, wherein said heptad has a sequence of the form $XnpXnp_1Xps_1Xnp_2Xnp_1Xps_1Xnp_2$; wherein each $Xps_1$ denotes a positively charged amino acid residue at physiological pH, and the two $Xps_1$ residues are residues of the same amino acid; wherein $Xnp_1$ denotes a nonpolar amino acid residue at physiological pH, and the two $Xnp_1$ residues are residues of the same amino acid; wherein $Xnp_2$ denotes a nonpolar amino acid residue at physiological pH, and the two $Xnp_2$ residues are residues of the same amino acid; and wherein $Xnp_1$ and $Xnp_2$ may be the same or different.

28. A process as recited in claim 1, wherein said heptad has a sequence of the form $XnpXps_1Xnp_1Xnp_2Xps_1Xnp_1Xnp_2$; wherein each $Xps_1$ denotes a positively charged amino acid residue at physiological pH, and the two $Xps_1$ residues are residues of the same amino acid; wherein $Xnp_1$ denotes a nonpolar amino acid residue at physiological pH, and the two $Xnp_1$ residues are residues of the same amino acid; wherein $Xnp_2$ denotes a nonpolar amino acid residue at physiological pH, and the two Xnp₂ residues are residues of the same amino acid; and wherein Xnp₁ and Xnp₂ may be the same or different.

29. A process for lysing bacteria in the presence of mammalian cells, wherein lysis of the bacteria occurs preferentially over the lysis of the mammalian cells; wherein said process comprises exposing the bacteria and mammalian cells to a lytic peptide at a concentration that causes lysis of the bacteria preferentially over lysis of the mammalian cells; wherein said lytic peptide comprises the 21-mer (KLGKKLG)₃ (SEQ ID NO. 21), or the 21-mer (KLGKLGK)₃ (SEQ ID NO. 38), or the 21-mer (KKLGKLG)₃ (SEQ ID NO. 42).

30. A process as recited in claim 29, wherein said lytic peptide comprises the 21-mer (KLGKKLG)₃ (SEQ ID NO. 21).

31. A process as recited in claim 29, wherein said lytic peptide comprises the 21-mer (KLGKLGK)₃ (SEQ ID NO. 38).

32. A process as recited in claim 29, wherein said lytic peptide comprises the 21-mer (KKLGKLG)₃ (SEQ ID NO. 42).

* * * * *